United States Patent
Pillai et al.

(10) Patent No.: US 9,623,529 B2
(45) Date of Patent: Apr. 18, 2017

(54) APPARATUS FOR CONDUCTING ORAL CARE EXPERIMENTS AND METHOD OF FORMING AND USING THE SAME

(75) Inventors: Shyamala Pillai, Piscataway, NJ (US); Guofeng Xu, Plainsboro, NJ (US)

(73) Assignee: Colgate-Palmolive, New York, NY (US)

( * ) Notice: Subject to any disclaimer, the term of this patent is extended or adjusted under 35 U.S.C. 154(b) by 289 days.

(21) Appl. No.: 13/992,267

(22) PCT Filed: Dec. 7, 2010

(86) PCT No.: PCT/US2010/059193
§ 371 (c)(1), (2), (4) Date: Jun. 7, 2013

(87) PCT Pub. No.: WO2012/078137
PCT Pub. Date: Jun. 14, 2012

(65) Prior Publication Data
US 2013/0249159 A1    Sep. 26, 2013

(51) Int. Cl.
| | | |
|---|---|---|
| B23Q 3/18 | (2006.01) | |
| A61C 19/10 | (2006.01) | |
| A61C 19/00 | (2006.01) | |
| A61C 19/04 | (2006.01) | |
| G09B 23/28 | (2006.01) | |

(52) U.S. Cl.
CPC ............ *B23Q 3/18* (2013.01); *A61C 19/00* (2013.01); *A61C 19/04* (2013.01); *A61C 19/10* (2013.01); *G09B 23/283* (2013.01); *Y10T 29/49567* (2015.01)

(58) Field of Classification Search
CPC .................................................... A61C 19/10
See application file for complete search history.

(56) References Cited

U.S. PATENT DOCUMENTS

| | | | | | |
|---|---|---|---|---|---|
| 74,971 | A | * | 3/1868 | Merritt .................. | A61C 19/10 206/83 |
| 1,431,159 | A | * | 10/1922 | Huff, Jr. ........................ | 206/83 |
| 1,442,081 | A | * | 1/1923 | Maeulen et al. ................ | 206/83 |

(Continued)

FOREIGN PATENT DOCUMENTS

| | | |
|---|---|---|
| DE | 19933018 | 1/2001 |
| GB | 170146 A * | 10/1921 |

(Continued)

OTHER PUBLICATIONS

Hodges, Elaine R.S. "The Guild Handbook of Scientific Illustration," Guild of Natural Science Illustrators. pp. 32-33. <https://books.google.com/books?id=gD8pWkA6TcwC&lpg=PA33&ots=atXCewpwzL&dq=specimen%20teeth%20wax&pg=PA32#v=onepage&q=specimen%20teeth%20wax&f=false>.*
Wang L1, Honorio HM, Rios D, Delbem AC, Palma-Dibb RG, Buzalaf MA, Atta MT, Tenuta LM. "Short-term in situ/ex vivo study of the anticariogenic potential of a resin-modified glass-ionomer cement associated with adhesive systems." NCBI. Nov. 2010. <http://www.ncbi.nlm.nih.gov/pubmed/20927415>.*

(Continued)

*Primary Examiner* — Joseph J Hail
*Assistant Examiner* — Joel Crandall

(57) ABSTRACT

An apparatus for conducting oral care experiments with enamel block substrates (140) and a method of forming and using the same. In one aspect, the invention can be an apparatus for conducting oral care experiments comprising: a plate having a first major surface (111) and a second major surface (112); a handle (170) coupled to and extending from the plate; and at least one enamel block substrate mounted on the first major surface of the plate.

15 Claims, 7 Drawing Sheets

(56) References Cited

U.S. PATENT DOCUMENTS

| | | | | |
|---|---|---|---|---|
| 1,634,687 | A * | 7/1927 | Sanders | 206/83 |
| 2,193,988 | A * | 3/1940 | Sheppard | 206/83 |
| 2,269,780 | A * | 1/1942 | Myerson | 206/83 |
| 3,111,760 | A * | 11/1963 | Semmelman et al. | 433/26 |
| 4,515,770 | A * | 5/1985 | Besic | A23G 3/36 127/29 |
| 4,566,466 | A | 1/1986 | Ripple et al. | |
| 4,629,424 | A | 12/1986 | Lauks et al. | |
| 5,853,704 | A | 12/1998 | Zhang et al. | |
| 6,471,946 | B1 | 10/2002 | Takatsuka et al. | |
| 6,517,815 | B1 * | 2/2003 | Leinen | A61K 8/24 424/49 |
| 6,733,818 | B2 | 5/2004 | Luo et al. | |
| 2001/0012509 | A1 * | 8/2001 | Mitra et al. | 424/49 |
| 2002/0061282 | A1 * | 5/2002 | Georgiades | 424/49 |
| 2002/0137000 | A1 * | 9/2002 | Eggler | 433/26 |
| 2003/0091959 | A1 * | 5/2003 | Shinozaki et al. | 433/167 |
| 2004/0002035 | A1 | 1/2004 | Jacobs et al. | |
| 2004/0005277 | A1 | 1/2004 | Willison et al. | |
| 2006/0222603 | A1 | 10/2006 | Kamasaka et al. | |
| 2008/0152600 | A1 * | 6/2008 | Huang | A61K 8/29 424/50 |
| 2008/0153054 | A1 * | 6/2008 | Masters et al. | 433/26 |
| 2009/0092565 | A1 | 4/2009 | Koyama et al. | |
| 2010/0304331 | A1 * | 12/2010 | Preti | A61C 19/10 433/172 |

FOREIGN PATENT DOCUMENTS

| | | |
|---|---|---|
| JP | H04-213059 | 8/1992 |
| WO | WO 02/002905 | 1/2002 |
| WO | WO 03/015656 | 2/2003 |
| WO | WO 2010/117753 | 10/2010 |

OTHER PUBLICATIONS

Hara AT, Ando M, Gonzalez-Cabezas C, Cury JA, Serra MC, Zero DT. Protective effect of the dental pellicle against erosive challenges in situ. Journal of Dental Research. 2006;85(7):612-616.*
Rios D, Hon6rio HM, Magalhaes AC, Buzalaf MA, Palma-Dibb RG, Machado MA, et al. Influence of toothbrushing on enamel softening and abrasive wear of eroded bovine enamel: an in situ study. Braz Oral Res. 2006;20:148-154.*
Trezuboy et at, 2007, Encyclopedia of Prosthodontics, Sankt-Petersburg FOLIANT p. 74-85.
Blake-Haskins et al., 1992, "Effect of calcium in model plaque on the anticaries activity of fluoride in vitro," J. Dental Research 71(8):1482-1486.
Cury et al., 2001, "In situ study of sucrose exposure, mutans streptococci in dental plaque and dental caries," Brazilian Dental J. 12(2):101-104.
Gron et al., 1969, "A study of inorganic constituents in dental plaque," J. Dental Research 48(5):799-805.
Ikemi et al., 1988, "Abrasion biopsy in studies of mineral density of experimental enamel lesions," J. Dental Research 67(2):508-514.
International Search Report and Written Opinion in International Application No. PCT/US10/059193, mailed Oct. 24, 2011.
Miyakawa et al., 2007, "Cavity generation in dental enamel using a copper-HyBrID laser," J. Mater. Sci: Mater. Med. 18:1507-1513.
Rios et al., 2006, "Influence of toothbrushing on enamel softening and abrasive wear of eroded bovine enamel: an in situ study, Pediatric Dentistry," Braz Oral Res. 20(2):148-154.
Shu et al., 2000, "Development of multi-species consortia biofilms of oral bacteria as an enamel and root caries model system," Arch. Oral Biol. 45(1):27-40.

* cited by examiner

APPARATUS FOR CONDUCTING ORAL CARE EXPERIMENTS AND METHOD OF FORMING AND USING THE SAME

FIELD OF THE INVENTION

The present invention relates generally to an apparatus and method for conducting oral care experiments, and specifically to an apparatus and method for conducting oral care experiments wherein one or more enamel block substrates are positioned within an oral cavity.

BACKGROUND OF THE INVENTION

In the oral care industry, it is difficult to gather experimental data on the teeth of a living person due to the vast number of inherent differences from one person's teeth to another, and the lack of a constant attribute upon which to base the data. As such, experimental data is typically collected by subjecting sterilized enamel block substrates to a condition, such as sugar or coffee, and then applying an oral care material, such as a dentifrice or a tooth whitening solution, to the enamel block substrates to determine the efficiency of the oral care material. In many experimental situations, it is also important to subject the enamel block substrates to saliva in order to form a salivary pellicle on the enamel block substrates. This reproduces the environmental conditions that teeth are subjected to within the mouth of a living person. Therefore, it has been known to mount enamel blocks to acrylic palatal appliances, which can then be inserted into the mouth of a user and worn.

Specifically, an acrylic palatal appliance, such as a retainer, is created to fit on the palate of a particular user. A typical acrylic palatal appliance is formed to fit a particular user and to rest securely against the inner surfaces of the user's upper teeth and remain in place against the palate of that user. Recesses are formed into the acrylic palatal appliance in which the enamel block substrates are disposed. Once created, the acrylic palatal appliance having the enamel block substrates mounted thereon is inserted into and removed from a user's mouth repetitively. Specifically, the acrylic palatal appliance can be inserted into a user's mouth to achieve salivary pellicle formation, removed from the user's mouth to subject the enamel block substrates to a particular oral care material or other substance, and then reinserted into the user's mouth to gather data regarding the effectiveness of the oral care material on the teeth within the environment of a user's mouth.

One major problem with using existing acrylic palatal appliances for experimental purposes is that every person has a different shape to their mouth. This requires that an acrylic palatal appliance be created that is particularly designed to be worn by a single individual. To create an acrylic palatal appliance, a technician must make an alginate impression of a user's mouth by placing a tray containing a powder comprising alginate salt, calcium salt and trisodium phosphate into the user's mouth. The powder hardens into a rubbery, gel-like substance upon mixing with the user's saliva and creates an impression of the user's mouth. A hard plaster is then poured into the gel-like impression, which makes a duplicate of the user's mouth and teeth. The hard plaster model must then be trimmed to get rid of extra plaster. After many intervening cleaning and preparing steps, acrylic can be poured into the hard plaster model in order to create the acrylic palatal appliance that is designed to fit the unique mouth of a single individual.

Thus, creating an acrylic palatal appliance is extremely time consuming and tedious. Moreover, requiring each person participating in an experimental study to have their own personal acrylic palatal appliance slows down the experimental process. Furthermore, an acrylic palatal appliance containing enamel block substrates for testing purposes cannot be reused by a second test participant even after sterilization because it will not fit that user's mouth. Additionally, many potential test participants are unwilling to wear an acrylic palatal appliance or have one made. This can make it difficult for an organization attempting to conduct an experimental study to obtain a sufficient number of willing participants in order to gather adequate data.

These problems require a better way to conduct oral care experiments on enamel block substrates both in-vivo and ex-vivo.

BRIEF SUMMARY OF THE INVENTION

The present invention is directed to an apparatus for conducting oral care experiments that utilizes enamel block substrates mounted on a plate and a method of forming and using the apparatus. The apparatus comprises a handle that is coupled to and extends from the plate to enable the plate to be held in a desired position either within or external to a user's mouth.

In one aspect, the invention can be an apparatus for conducting oral care experiments comprising: a plate having a first major surface and a second major surface; a handle coupled to and extending from the plate; and at least one enamel block substrate mounted on the first major surface of the plate.

In another aspect, the invention can be a method of forming an apparatus for conducting oral care experiments comprising the steps of: a) forming a plate having a first major surface and a second major surface; b) mounting at least one enamel block substrate on the first major surface of the plate; and c) coupling a handle to the plate, the handle extending from the plate.

In yet another aspect, the invention can be a method of subjecting at least one enamel block substrate to an oral cavity for gathering data on effects of an oral care material on the at least one enamel block substrate comprising: a) providing an oral care material to an oral cavity; b) providing an apparatus comprising: a plate having a first major surface and a second major surface; a handle coupled to and extending from the plate; and at least one enamel block substrate mounted on the first major surface of the plate; and c) inserting the plate having the at least one enamel block substrate mounted thereon into the oral cavity for a predetermined period of time.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
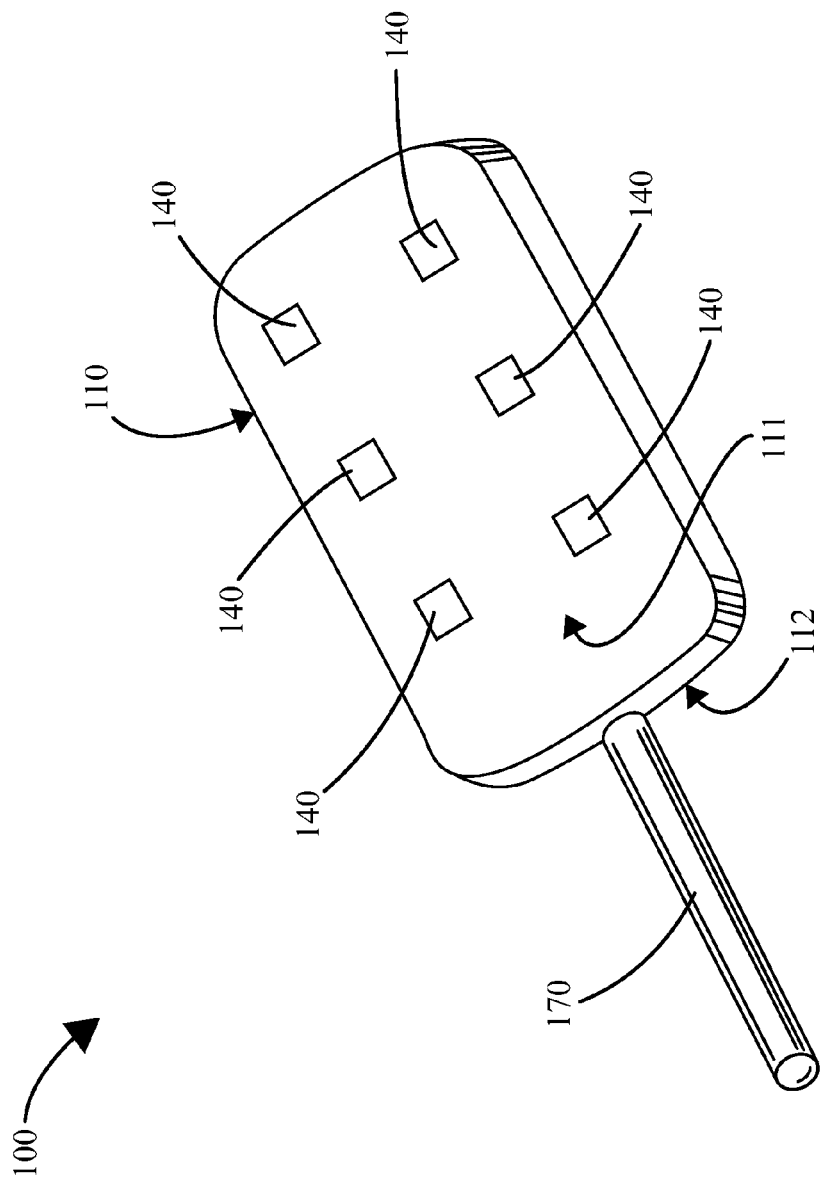
FIG. 1 is a perspective view of an apparatus for conducting oral care experiments in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of the exemplary embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," "secured" and similar refer to a relationship wherein structures are secured or attached to one another either directly or indirectly through intervening structures, as well as both movable or rigid attachments or relationships, unless expressly described otherwise. Moreover, the features and benefits of the invention are described by reference to the exemplary embodiments illustrated herein. Accordingly, the invention expressly should not be limited to such exemplary embodiments, even if indicated as being preferred. The discussion herein describes and illustrates some possible non-limiting combinations of features that may exist alone or in other combinations of features. The scope of the invention is defined by the claims appended hereto.

Referring now to FIG. 1, an enamel block appliance 100 for conducting oral care experiments according to one embodiment of the present invention is illustrated. The enamel block appliance 100 can be used for in-vivo and/or ex-vivo oral care experimentation. As will be described in greater detail below, the enamel block appliance 100 generally takes the form of a lollipop and, in certain embodiments, is similar in size and shape to a lollipop. However, it will be understood that the enamel block appliance 100 is not limited to the particular shapes and sizes described herein and other shapes and sizes can be used as will become apparent from the description below. The enamel block appliance 100 is easy and quick to assemble and is not user specific in size and/or shape so that the enamel block appliance 100 can be used by more than one person after proper sterilization between uses. Moreover, the size and shape of the enamel block appliance 100 is selected so that it can be used universally between test subjects.

The enamel block appliance 100 generally comprises a plate 110, a plurality of enamel block substrates 140 and a handle 170. Although the enamel block appliance 100 is illustrated and described as having a plurality of enamel block substrates 140 mounted on the plate 110, there may be only one enamel block substrate 140 mounted on the plate 110 in certain embodiments. Stated simply, the enamel block appliance 100 comprises at least one enamel block substrate 140 mounted on the plate 110 in the manner described below.

As will be described in detail below, the enamel block substrates 140 are mounted on the plate 100 in such a manner that one surface of the enamel block substrates 140 is exposed to the ambient environment and the other surface of the enamel block substrates 140 is bonded to the plate 110. The enamel block substrates 140 are preferably mounted on the plate 110 and arranged in an array. Although FIG. 1 illustrates six enamel block substrates 140 mounted in a three-by-two array, more or less than six enamel block substrates 140 may be used and mounted in different arrangements. In certain embodiments, the array contains X rows and Y columns of enamel block substrates such that X and Y are both integers that are greater than two. In certain specific embodiments, the array may be a three-by-two array (illustrated in FIG. 1) or a four-by-three array (not illustrated). Of course, the array can have any number of columns and rows as desired.

The exemplified embodiment of the plate 110 has a generally rectangular shape with rounded corners. Of course, the invention is not so limited and the plate 110 may take on any other desired shape. However, in certain embodiments, the plate 110 is free of sharp edges and/or sharp corners in order to ensure comfort when the plate 110 is inserted into the mouth of a user, as will be described in more detail below.

The plate 110 has a first major surface 111 and a second major surface 112 that is opposite the first major surface 111. Furthermore, as illustrated in FIG. 1, the plate 110 is substantially flat. The flat structure of the plate 110 enhances comfort when the plate 110 is inserted into the mouth of a user and provides flexibility so that the plate 110 can conform to the contours of the mouth as may be necessary in certain experimental situations.

In some embodiments, the first major surface 111 and the second major surface 112 are substantially parallel to one another. Although the parallel structure may be obtained with the substantially flat plate arrangement, the parallel structure may also be obtained when the plate 110 is not flat, such as when the first and second major surfaces 111, 112 are both contoured in a corresponding manner so as to be parallel to one another. In one embodiment, the plate 110 has a thickness in a range of 0.15 cm to 1 cm, and in a specific embodiment a thickness of 0.2 cm. Of course, the invention is not so limited and the plate 110 may have other thicknesses as would be understood by persons skilled in the art.

The plate 110 is formed of a material that is inert to saliva. In certain embodiments, the plate 110 is formed of a material that is inert both to saliva and to the oral care material to be tested using the enamel block appliance 100. In one embodiment, the plate 110 is formed of a pliable or compressible material. In one preferable embodiment, the pliable material is a heat-sensitive material that becomes more pliable upon being heated, such as a wax material. Examples of the types of wax materials that may be used in the present invention include, without limitation, an animal wax, a vegetable wax, a mineral wax, a petroleum wax, a synthetic wax and/or combinations thereof. Dental wax, which is typically formed as a combination of two or more of the wax types described above, is preferable. Of course, the invention is not limited to a plate formed of a pliable material and the plate 110 may be formed of other materials. Other suitable materials include polymeric, plastic, metal, and/or combinations thereof.

Furthermore, as used herein, the term "oral care material" can refer to any type of material that is currently used or being tested for use as a product to benefit the oral health of the dentiture including the teeth, tongue and gums. This can include, without limitation, tooth whitening substances, dentifrice, mouthwash, any materials having special flavors, tooth numbing materials, anti-sensitive materials or various known or later discovered medicaments. Furthermore, an oral care material may be a material that contains an active agent. Non-limiting examples of active agents which can be used include antibacterial agents, whitening agents, anti-sensitivity agents, anti-inflammatory agents, anti-attachment agents, plaque indicator agents, flavorants, sensates, breath freshening agents, gum health agents and colorants. Examples of these agents include metal ion agents (e.g., stannous ion agents, copper ion agents, zinc ion agents, silver ion agents) triclosan; triclosan monophosphate, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride (TDEPC), octenidine, delmopinol, octapinol, nisin, essential oils, furanones, bacteriocins, flavans, flavinoids, folic acids, vitamins, minerals, hydrogen peroxide, urea peroxide, sodium percarbonate, PVP-H2O2, polymer-bound peroxides, potassium nitrates, occluding agents, bioactive glass, arginine salts, arginine bicarbonate, bacalin, polyphenols, ethyl pyruvate, guanidinoethyl disulfide, tartar control agents, anti-stain ingredients, phosphate salts, polyvinylphosphonic acid, PVM/MA copolymers; enzymes, glucose oxidase, papain, ficin, ethyl lauroyl arginate, menthol, carvone, and anethole, various flavoring aldehydes, esters, and alcohols, spearmint oils, peppermint oil, wintergreen oil, sassafras oil, clove oil, sage oil, eucalyptus oil, marjoram oil, cinnamon oil, lemon oil, lime oil, grapefruit oil, and/or orange oil. Of course, the invention is not to be limited and any substance, the effects of which is desired to be tested when applied to the teeth of a user, can be used as the oral care material. The specific oral care material that may be experimentally tested using the enamel block appliance 100 is in no way limiting of the present invention.

The enamel block substrates 140 are mounted on the first major surface 111 of the plate 110. A few possible mounting procedures are described in detail below with reference to FIGS. 2a-2d. In one embodiment, the enamel block substrates 140 can be slices of the crown of a tooth that are typically cut with a diamond core drill. After cutting, the slices are ground flat and polished with a rotary polishing wheel. Of course, the type of machinery or equipment used to create the enamel block substrates 140 are not limiting of the present invention. Additional suitable examples of enamel block substrates include bovine tooth, a human tooth, a porcelain tooth, a HAP (hydroxy apatite) disc or any other real or artificial surface or material that would be effective for testing the effects of various oral care materials on teeth.

Figure 2A:
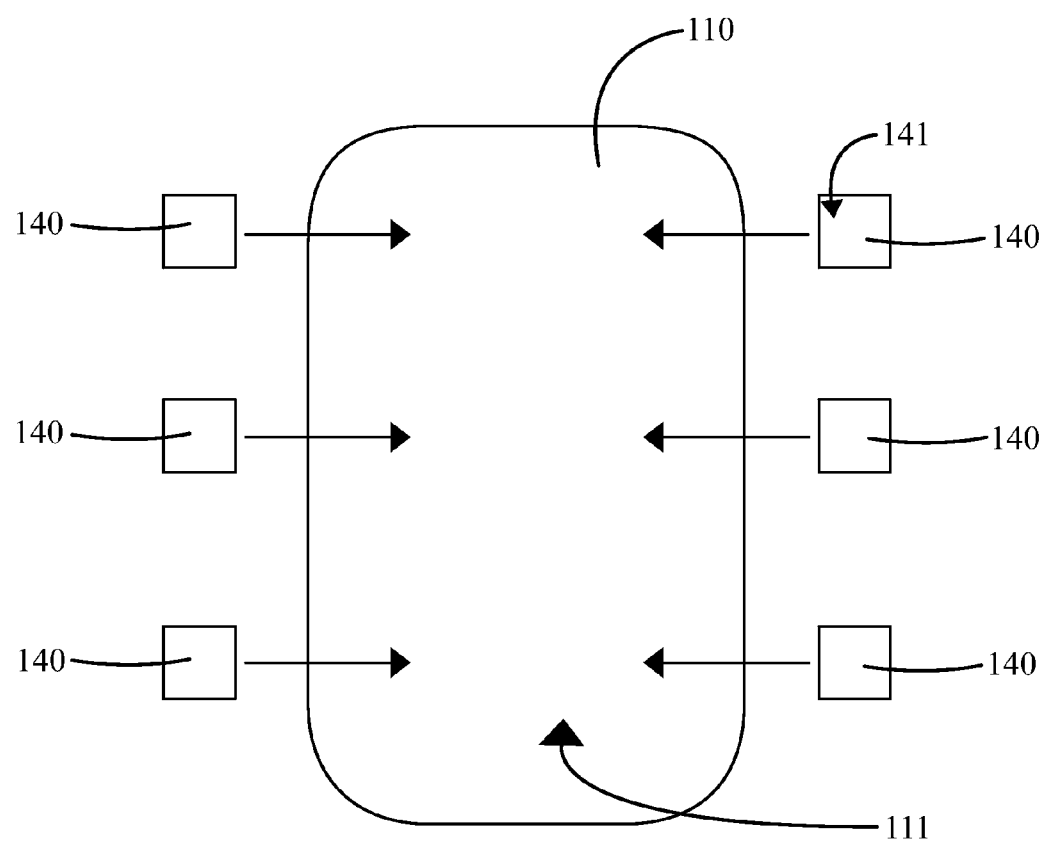
FIG. 2a is a schematic of the apparatus of FIG. 1 schematically illustrating the mounting of enamel block substrates to the plate, in accordance with an embodiment of the present invention.
Figure 2B:
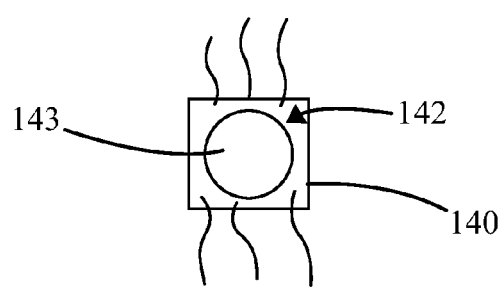
FIG. 2b is a rear view of an enamel block substrate with a mass of heated wax material provided thereon in order to effectuate mounting of the enamel block substrate to the plate, in accordance with an embodiment of the present invention.
Figure 2C:
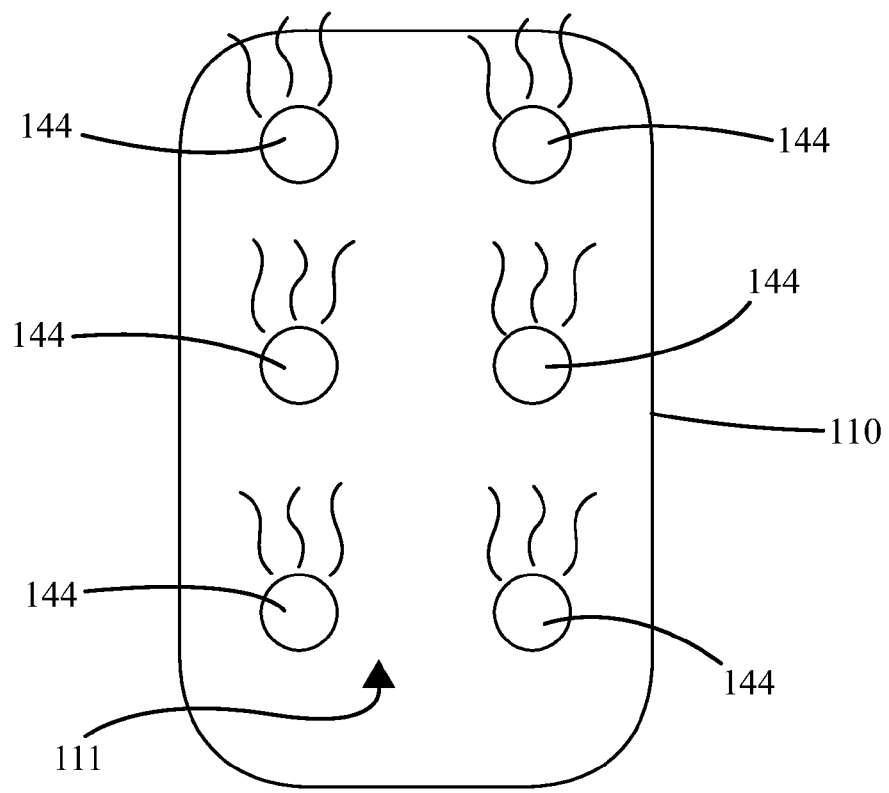
FIG. 2c is a front view of the plate of the apparatus of FIG. 1 with a mass of heated wax material provided thereon.

Referring now to FIG. 2a, a schematic of the plate 110 with arrows indicating the relative mounting positions of the enamel block substrates 140 is illustrated. FIG. 2a illustrates the preferable embodiment described above with a three-by-two array of enamel block substrates 140 on the first major surface 111 of the plate 110. Of course, any arrangement of the enamel block substrates 140 on the plate 110 is possible, including a random mounting pattern. Furthermore, as discussed above, the enamel block appliance 100 may only include one enamel block substrate 140 in certain embodiments.

Referring to FIGS. 2a-2d, the formation of the enamel block appliance 100 in accordance with one embodiment of the invention will be described. When the enamel block appliance 100 is assembled, each of the enamel block substrates 140 have a front surface 141 that is exposed to the ambient environment and a rear surface 142 that is bonded to the first major surface 111 of the plate 110. Each of the enamel block substrates 140 further comprise a perimetric edge 146 collectively formed by the top, bottom and side edges of the enamel block substrates 140. Although the enamel block substrates 140 are illustrated as generally rectangular structure having four edges, the enamel block substrates 140 may take on any other shapes, including oval or any other polygon or irregular shape.

In one preferred embodiment of the present invention, the enamel block substrates 140 are mounted to the plate 110 by first applying mass of heated wax material 143 to the rear surface 142 of each of the enamel block substrates 140. While the mass of heated wax material 143 is still hot, the rear surface 142 of the enamel block substrates 140 are pressed against the first major surface 111 of the plate 110 so that the first mass of heated wax material 143 bonds the enamel block substrates 140 to the first major surface 111 of the plate 140.

In embodiments where the plate 110 is made of a wax material, such as a wax sheet having opposing major surfaces, the mass of heated wax material 143 on the rear surface 142 of the enamel block substrate 140 readily bonds to the wax material of the plate 110 as it cools. Initially, as this mass of heated wax material 143 comes into contact with the wax material of the plate 140, the heat is transferred from the mass of heated wax material 143 to the wax material of the plate 110, which softens the wax material of the plate 110. This allows the first mass of heated wax material 143 and the wax material of the plate 110 to cool and harden, thereby forming a unitary structure. This provides an extremely efficient and effective method of mounting the enamel block substrates 140 to the plate 110.

Additionally or alternatively, a second mass of heated wax material 144 may be provided directly onto the first major surface 111 of the plate 110 at locations where it is desired to mount enamel block substrates 140. This can be done by heating a separate mass of wax and applying it to the plate 110 or, in embodiments where the plate is formed of a wax material, heating an area of the plate 110 itself. While the second mass of heated wax material 144 is still hot, the rear surfaces 142 of the enamel block substrates 140 are pressed against the first major surface 111 of the plate 110 so that the second mass of heated wax material 144 bonds the enamel block substrates 140 to the first major surface 111 of the plate 140. Providing the first mass of heated wax material 143 onto the rear surface 142 of the enamel block substrates 140 and the second mass of heated wax material 144 onto the first major surface 111 of the plate 110 will enhance the bonding of the enamel block substrates 140 to the plate 110. This enhanced bonding occurs because the first and second masses of heated wax material 143, 144 will intermix and bond together while hardening, thereby forming a unitary structure.

As mentioned above, an alternative to providing the second mass of heated wax material 144 onto the first major surface 111 of the plate 110, portions of the first major surface 111 of the plate 110 can be heated directly. When the plate 110 is formed of a wax material, heating the actual material of the plate 110 will have the same effect as providing an additional mass of heated wax material onto the plate 110.

Figure 2D:
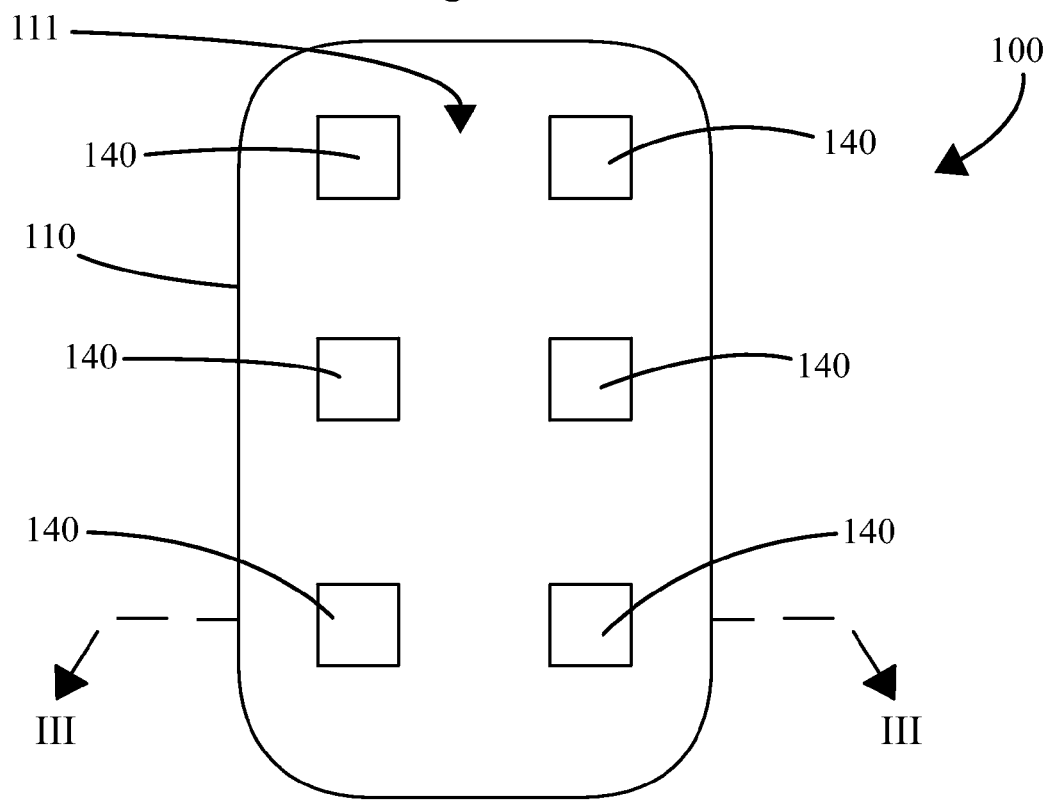
FIG. 2d is a front view of the apparatus of FIG. 1 with the enamel block substrates mounted thereon.

After one or both of the masses of heated wax material 143, 144 are provided and the enamel block substrates 140 are pressed against the first major surface 111 of the plate 110, the enamel block substrates 140 are mounted to the first major surface 111 of the plate 110 by pressing the enamel block substrates 140 in place. The resultant structure is illustrated in FIG. 2d as the enamel block appliance 100 without the handle 170.

It should be noted that although the formation of the enamel block appliance 100 is described above using masses of heated wax material as the bonding agent, other materials and/or substances can be used to bond the enamel block substrates 140 to the plate 110. Specifically, the enamel block substrates 140 may be bonded to the plate 110 by adhesives such as thermoplastic adhesives, light-curing adhesives, drying adhesives, pressure sensitive adhesives, hot adhesives, reactive adhesives, natural adhesives, synthetic adhesives and the like. The type of adhesive used should be non-toxic and capable of maintaining the bond between the enamel block substrates 140 and the plate 110 in both wet and dry environments. This can be any adhesive that is currently known or later discovered that can create or maintain a strong bond between two or more separate structures in a wet environment. Wax is one preferable bonding agent because it maintains its bonding qualities in both wet and dry environments and the enamel block appliance 100 of the present invention is intended for use in both wet and dry environments.

The terms soften and melt may be used interchangeably throughout the present application. For example, the resultant effect of applying heat or thermal energy to a wax material can be described as softening or melting the wax material. However, the plate 110 is not limited to being formed of wax materials. Thus, the plate 110 can be formed of other pliable materials that soften, melt or become more pliable when subjected to heat or other thermal energy. It should be understood that in further embodiments, the plate 110 does not need to be formed of a pliable material but can be formed of a rigid and/or elastomeric material, such as polyethylene, polypropylene (PP), polyamide, polyester, cellulosics, SAN, acrylic, ABS, thermoplastic elastomers, stainless steel, metal and/or combinations thereof. Additionally, where a non-pliable material is used, to create the plate 110, such as a metal or rigid plastic, the enamel block substrates 140 may be press fit into openings on the plate instead of using a melting technique or adhesives. More specifically, the plate 110 may have several openings on the first major surface 111. The openings can sized to be slightly smaller than the enamel block substrates 140 so that by press fitting the substrate 140 onto the plate 110 at the openings, the enamel substrate is inserted into the opening and secured by the press fit. The openings can be tapered to receive the substrate 140 more easily.

Referring to FIGS. 3a-3d, the enamel block substrates 140 are illustrated mounted on and bonded to the plate 110. In the exemplified embodiment, the enamel block substrates 140 are mounted on the plate 110 so that the rear surface 142 of the enamel block substrates 140 rest atop the first major surface 111 of the plate 110. The adhesive layer that bonds the enamel block substrates 140 to the first major surface 111 of the plate 110 is not illustrated, but would be positioned between the enamel block substrates 140 and the first major surface 111 of the plate 110, and is a wax material in certain embodiments.

Figure 3A:
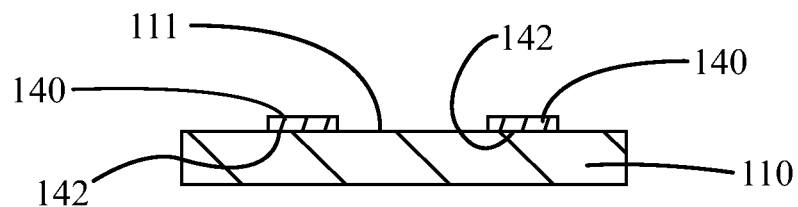
FIG. 3a is a transverse cross-sectional view of FIG. 2d taken along the line III-III.
Figure 3B:
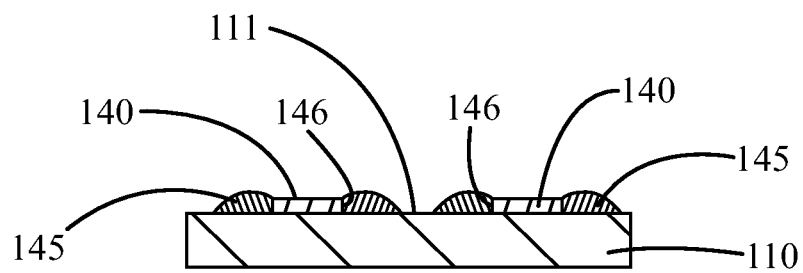
FIG. 3b is the transverse cross-sectional view of FIG. 3a with a retaining wall substantially surrounding the enamel block substrates.

Referring to FIG. 3b, in one embodiment, a retaining wall 145 protrudes from the first major surface 111 of the plate 110. The retaining wall 145 substantially surrounds the perimetric edge 146 of the enamel block substrates 140. In one embodiment, the retaining wall 145 is formed of a wax material. In such an embodiment, the retaining wall 145 may be created by the excess wax material from the first and/or second masses of heated wax material 143, 144 being pressed out from between the enamel block substrates 140 and the first major surface 111 of the plate 110 during the mounting process. Of course, the invention is not so limited and the retaining wall 145 may be formed by at least partially embedding the enamel block substrates 140 into the first major surface 111 of the plate 110, or by other means.

The retaining wall 145 protrudes from the first major surface 111 of the plate 110 a distance further than the top surface 141 enamel block substrates 140. Thought of another way, the top surface 141 of the enamel block substrates 140 are recessed relative to a top edge of the retaining wall 145. Conceptually, a basin is formed such that the top surface 141 of the enamel block substrates 140 forms a floor of the basin and the portions of the retaining wall 145 that extend upwardly from the enamel block substrates 140 form the wall of the basin. In this way, saliva and oral care material that comes into contact with the enamel block substrates 140 will remain in contact with the enamel block substrates 140. In such an embodiment, the retaining wall 145 acts as a barrier that traps saliva and oral care material within the basin and prevents saliva and oral care material from disengaging from the enamel block substrates 140.

Figure 3C:
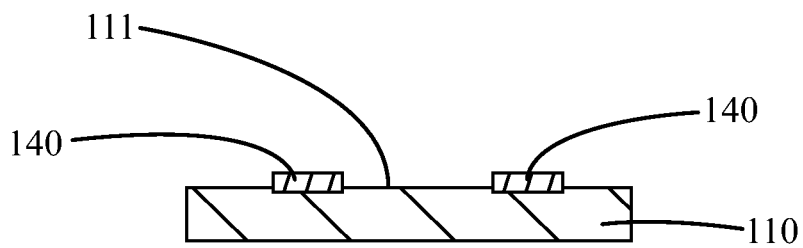
FIG. 3c is the transverse cross-sectional view of FIG. 3a with the enamel block substrates partially embedded into the front surface of the plate.

Referring to FIG. 3c, another embodiment showing the enamel block substrates 140 mounted on the plate 110 is illustrated. In this embodiment, the enamel block substrates 140 are partially embedded in the first major surface 111 of the plate 110. Although the enamel block substrates 140 are illustrated as only being partially embedded in the first major surface 111 of the plate 110, the enamel block substrates 140 may be fully embedded so that the enamel block substrates 140 are depressed or flushed relative to the first major surface 111 of the plate 110.

Figure 3D:
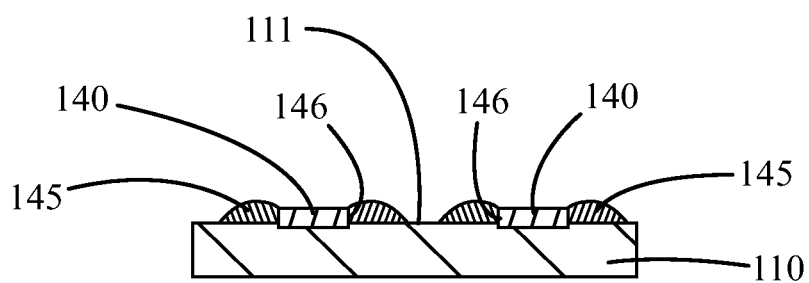
FIG. 3d is the transverse cross-sectional view of FIG. 3c with a retaining wall substantially surrounding the enamel block substrates.

Referring to FIG. 3d, the retaining wall 145 is illustrated surrounding the perimetric edge 146 of the partially embedded enamel block substrates 140. By partially embedding the enamel block substrates 140, the enamel block substrates 140 are depressed a greater amount relative to the retaining wall 145 than they would otherwise be as described above with regard to FIG. 3b.

Figure 4A:
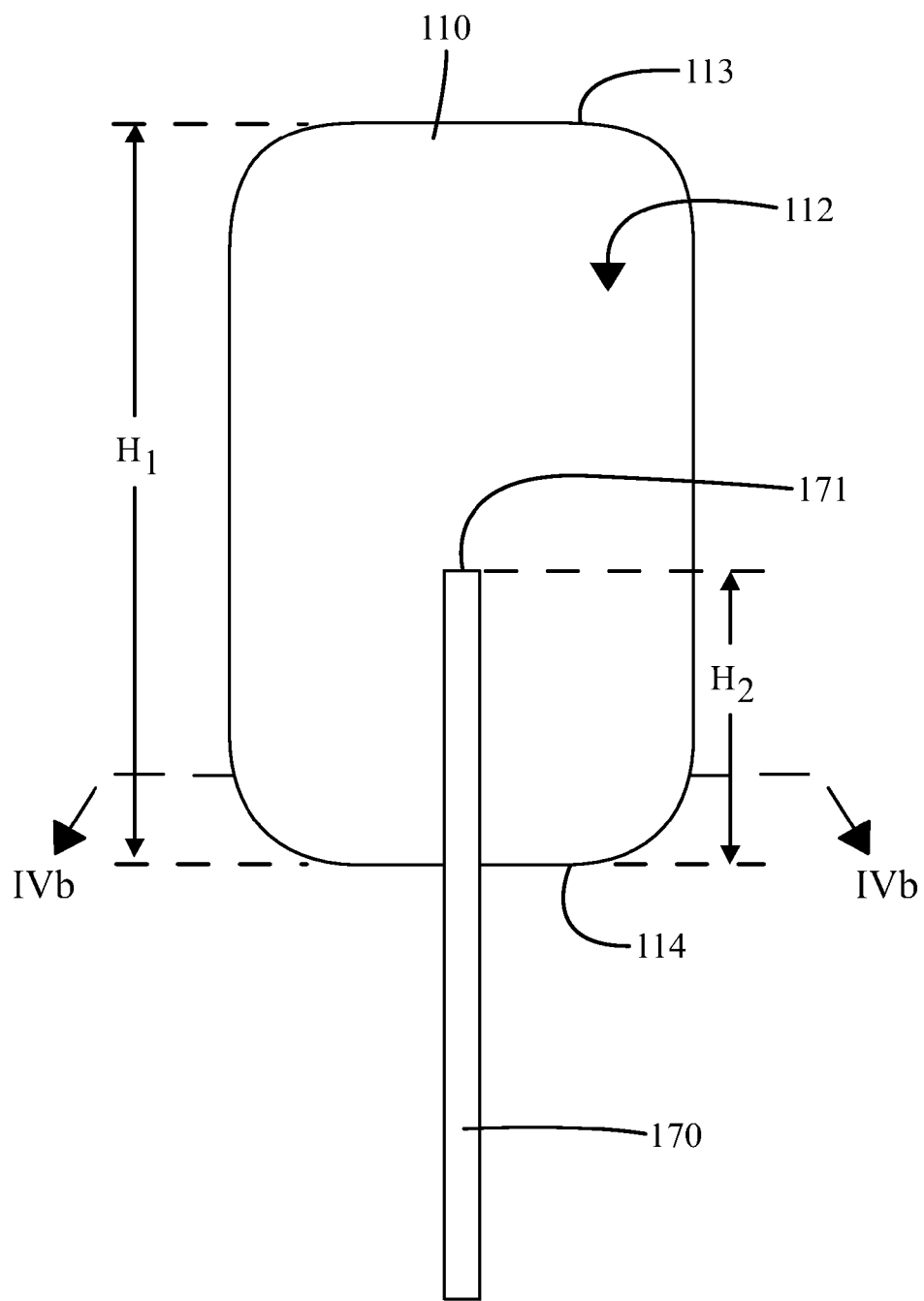
FIG. 4a is a rear view of the plate of the apparatus of FIG. 1 with the handle coupled to and extending from the plate.
Figure 4B:
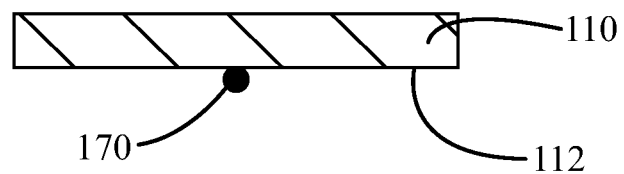
FIG. 4b is a transverse cross-sectional view of FIG. 4a taken along the line IVb-IVb.
Figure 4C:
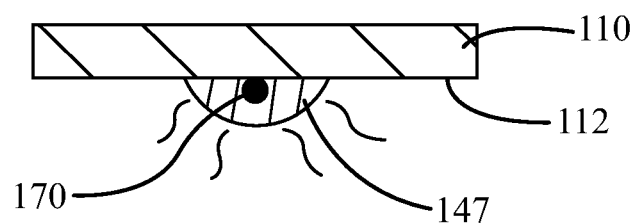
FIG. 4c is the transverse cross-sectional view of FIG. 4b with a layer of wax covering a portion of the handle and a portion of the second major surface of the plate.

Referring now to FIGS. 4a-4c, the attachment of the handle 170 to the plate 110 will be described. The handle 170 may be an elongated member, such as an elongated rod-like structure, in order to enhance manipulation of the plate 110 within and external to a user's mouth. Although the handle 170 is illustrated as an elongate member, the invention is not so limited and the handle 170 can take on any shape and size as long as the handle 170 is capable of manipulating the plate 110 into various angles either within or external to a user's mouth.

The handle 170 is coupled to and extends from the plate 110. In the illustrated embodiment, the handle 170 is coupled to the second major surface 112 of the plate 110 which is opposite the first major surface 111. As such, the handle 170 is coupled to the plate 110 on the opposite side of the plate 110 as the enamel block substrates 140. However, the invention is not so limited and the handle 170 may be coupled to the first major surface 111 of the plate 110, or the handle 170 may be embedded in the plate 110 so as to be between the first and second major surfaces 111, 112 of the plate 110.

Figure 5:
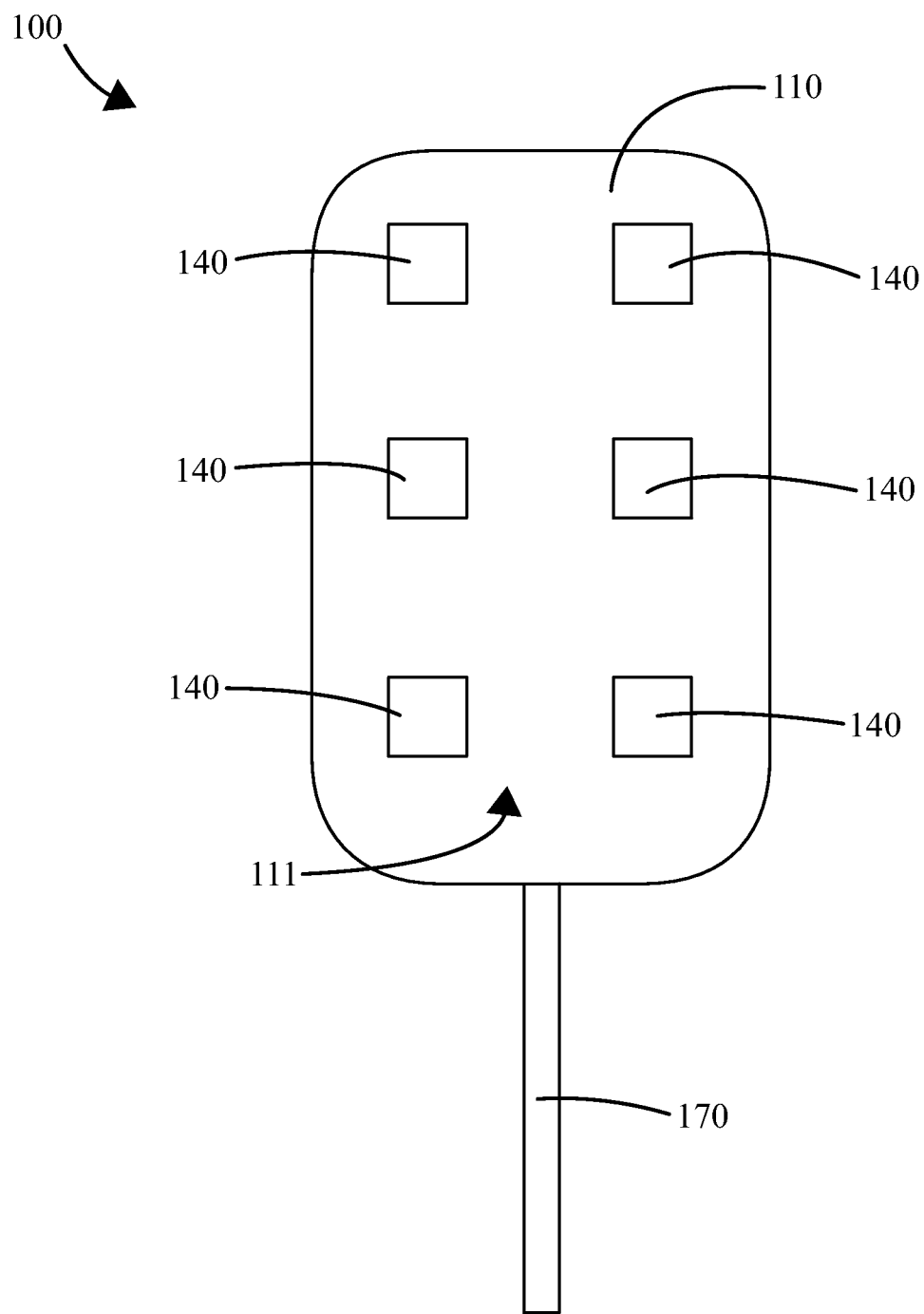
FIG. 5 is a front view of the apparatus of FIG. 1.

The handle 170 can be coupled to the plate 110 in any known manner. However, because the enamel block appliance 100 will be used under wet conditions, it is preferable that the coupling be done so as to enable the handle 170 to remain coupled to the plate 110 even under wet conditions. In one embodiment, the handle 170 is aligned on the second major surface 112 of the plate 110 and a layer of wax 147 is made to cover at least a portion of the handle 170 and a portion of the second major surface 112 of the plate 110. When the plate 110 is made of a wax material, the layer of wax 147 is then heated to form a unitary structure with the plate 110. This bonds the handle 170 between the second major surface 112 of the plate 110 and the layer of wax 147. Wax is an efficient bonding agent because wax is hydrophobic and the handle 170 will remain attached to the plate 110 even under wet conditions. Of course, other methods of attaching the handle 170 to the plate 110 are within the scope of the invention as would be understood to persons skilled in the art. The methods of adhesion bonding discussed above with regard to mounting the enamel block substrates 140 on the plate 110 are similarly applicable to the coupling of the handle 170 to the plate 110. FIG. 5 illustrates the enamel block appliance 100 after the enamel block substrates 140 are mounted to the plate 110 and the handle 170 is coupled to the plate 110.

By coupling the plate 110 to the handle 170, the enamel block substrates 140 can be subjected to different areas within a user's mouth. The handle 170 enables a user to manipulate the plate 110 so that the enamel block substrates 140 are subjected to the back of the mouth near the molars, the palate, the tongue, the area of the mouth adjacent the inner surface of the cheek, the teeth or any other area within the mouth that is desired to be tested. The handle 170 enables a user to manipulate the enamel block appliance 100 in an unlimited number of angles and positions with the user's mouth.

The plate 110 has a first height H1 defined as the distance between a top edge 113 of the plate 110 and a bottom edge 114 of the plate 110. Furthermore, a second height H2 is defined between the bottom edge 114 of the plate 110 and a top edge 171 of the handle 170. The second height H2 is preferably approximately one-third of the first height H1 so that the handle 170 is coupled to the plate 110 at a distance approximately one-third the first height H1 of the plate 110. Of course, the invention is not so limited and the handle 170 can be coupled to the plate 110 at other distances and heights as would be understood to persons skilled in the art.

The handle 170 is preferably formed of a rigid core of material that is coated by a wax material. More preferably, the rigid core is a tightly-wrapped paper material and it is then coated with a fine layer of wax. Of course, the invention is not so limited and the handle 170 may be formed of any other materials such as, for example, wood, metal, metal alloys, carbon fiber, thermoplastics and the like. The material of the handle 170 is preferably selected so that the handle 170 is able to maintain its structural integrity under both wet and dry conditions.

The enamel block appliance 100 can be used in a wide variety of experimental conditions. However, the enamel block appliance 100 is particularly suited for short internal experimentation. Short internal experimentation is intended to mean that the enamel block appliance 100 is only intended to be positioned within a user's mouth for short periods of time and it is not particularly suitable for overnight use. In some experimental situations, a user will apply an oral care material to the desired oral surface. After completion of the application, the enamel block appliance 100 is inserted into the user's mouth for a predetermined period of time. This type of an experiment can test the lingering effects of an oral care material on the environment within the mouth of a user or test participant after a brushing session.

Referring to FIGS. 1-5 concurrently, a method of subjecting at least one enamel block substrate to an oral cavity for gathering data on the effects of an oral care material on the at least one enamel block substrate will be described. In a preferable use, an oral care material is first provided to an oral cavity of a user. The oral care material can be any of the oral care materials described above, or any other oral care material that is desired to be experimentally tested for effects on an enamel block substrate. The oral care material can be provided to the oral cavity of the user via an oral care implement, such as a toothbrush, or in any other way as would be known to persons skilled in the art.

After the oral care material is adequately applied to the oral cavity, the enamel block appliance 100 described above is provided. The enamel block appliance 100 comprises the plate 110 having at least one enamel block substrate 140 mounted on the first major surface of the plate 110 and the handle 170 coupled to and extending from the plate 110.

The enamel block appliance 100 is then inserted into the oral cavity of the user as follows. The user grips the handle 170 of the enamel block appliance 100 and positions the plate 110 having the at least one enamel block substrate 140 mounted thereon into the oral cavity for a predetermined period of time. The enamel block appliance 100 of the present invention is typically used for short interval experimentation. Thus, the predetermined period of time is typically in the range of 2 minutes to 2 hours.

When using the enamel block appliance 100 as described above, it is preferable that the handle 170 is an elongate handle so that the plate 110 is easy to manipulate within the user's oral cavity. By using an elongate handle 170, a portion of the elongate handle 170 will protrude from the oral cavity when the plate 110 having the at least one enamel block substrate 140 mounted thereon is inserted into the oral cavity. Thus, the plate 110 will be positioned within the user's oral cavity and the elongate handle 170 will extend from the plate 110 to an area external to the user's oral cavity so that it can be gripped and manipulated by the user's hand. This will enable the user to position the plate 110 having the at least one enamel block substrate 140 mounted thereon in various locations within the user's mouth. As discussed above, the plate 110 can be manipulated to be positioned at the back of the mouth near the molars, the palate, the tongue, the area of the mouth adjacent the inner surface of the cheek, the teeth or any other desired area within the oral cavity.

It should be understood that although the enamel block appliance 100 is described as being used in the manner above, the enamel block appliance 100 may be used in any other manner known to persons skilled in the art. For example, the enamel block appliance 100 can be used for ex-vivo experimentation such that the enamel block appliance 100 is subjected to oral care materials or other conditions, but not subject to a user's oral cavity. Persons skilled in the art would be familiar with the many different potential uses of the enamel block appliance 100 of the present invention.

While a number of embodiments of the current invention have been described and illustrated in detail, various alternatives and modifications will become readily apparent to those skilled in the art without departing from the spirit and scope of the invention. As various changes could be made in the above methods, compositions and structures without departing from the scope of the invention, it is intended that all matter contained in this application, including all mechanisms and/or modes of interaction described above, shall be interpreted as illustrative only and not limiting in any way the scope of the appended claims.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

What is claimed is:

1. An apparatus for conducting oral care experiments comprising:
    a plate having a first major surface and a second major surface;
    an elongated rod-shaped handle coupled to and extending from the plate, the handle comprising a rigid core and a coating of wax material substantially covering the handle; and
    at least one enamel block substrate mounted on the first major surface of the plate, wherein the plate is formed of a material selected from the group consisting an animal wax, a vegetable wax, a mineral wax, a petroleum wax, a synthetic wax and combinations thereof;
    wherein the material is inert with respect to saliva;
    wherein the plate is substantially flat and the plate has a thickness of 0.15 cm to 1 cm;
    wherein a plurality of enamel block substrates are mounted on the first major surface of the plate and arranged in an array, the enamel block substrates each having a mass of heated wax material applied to a surface of the substrate to be pressed against the first major surface of the plate, and
    wherein the elongated rod-shaped handle includes a diameter that is substantially smaller than a width of the plate.

2. The apparatus according to claim 1 wherein the first major surface and the second major surface of the plate are substantially parallel to one another.

3. The apparatus according to claim 1 wherein the plate is formed of a wax material and the handle is coupled to the second major surface of the plate by a layer of a wax material that covers at least a portion of the handle and a portion of the second major surface of the plate.

4. The apparatus according to claim 3 wherein the layer of the wax material is heated to form a unitary structure with the plate.

5. The apparatus according to claim 1 wherein the enamel block substrate is selected from the group consisting of a bovine tooth, a human tooth, a porcelain tooth and a HAP disc.

6. The apparatus according to claim 1 wherein the enamel block substrate comprises a front surface and a rear surface, and wherein the enamel block substrate is mounted to the first major surface of the plate by providing a mass of a heated wax material to the rear surface of the enamel block substrate and pressing the enamel block substrate against the first major surface of the plate, the mass of heated wax material bonding the enamel block substrate to the first major surface of the plate.

7. The apparatus according to claim 1 wherein the enamel block substrate is mounted by positioning the enamel block substrate against the first major surface of the plate, heating the plate to soften a portion of the plate adjacent a perimetric edge of the enamel block substrate, and applying pressure to the enamel block substrate to at least partially embed the enamel block substrate in the first major surface of the plate.

8. The apparatus according to claim 1 further comprising a retaining wall protruding from the first major surface and substantially surrounding a perimetric edge of the enamel block substrate.

9. The apparatus according to claim 1 wherein the array is a three by two array or a four by three array.

10. The apparatus according to claim 1 wherein the plate is constructed of a pliable material.

11. The apparatus according to claim 10 wherein the pliable material is a heat-sensitive material that becomes more pliable upon being heated.

12. The apparatus according to claim 1, wherein the second major surface is at least partially exposed.

13. A method of forming an apparatus for conducting oral care experiments comprising the steps of:
    forming a plate having a first major surface and a second major surface;
    mounting at least one enamel block substrate on the first major surface of the plate; and
    coupling an elongated rod-shaped handle to the plate, the handle extending from the plate, the handle comprising a rigid core and a coating of wax material substantially covering the handle,
    wherein the plate is formed of a material selected from the group consisting of animal wax, a vegetable wax, a mineral wax, a petroleum wax, a synthetic wax and combinations thereof; wherein the material is inert with respect to saliva;
    wherein the plate is substantially flat and the plate has a thickness of 0.15 cm to 1 cm;
    wherein a plurality of enamel block substrates are mounted on the first major surface of the plate and arranged in an array, the enamel block substrates each having a mass of heated wax material applied to a surface of the substrate to be pressed against the first major surface of the plate; and
    wherein the elongated rod-shaped handle includes a diameter that is substantially smaller than a width of the plate.

14. A method of gathering data comprising:
a) providing an apparatus for conducting oral care experiments comprising:
   a plate having a first major surface and a second major surface;
   an elongated rod-shaped handle coupled to and extending from the plate, the handle comprising a rigid core and a coating of wax material substantially covering the handle; and
   at least one enamel block substrate mounted on the first major surface of the plate; and
b) positioning the apparatus in an oral cavity of a subject,
   wherein the plate is formed of a material selected from the group consisting of an animal wax, a vegetable wax, a mineral wax, a petroleum wax, a synthetic wax and combinations thereof;
   wherein the material is inert with respect to saliva;
   wherein the plate is substantially flat and the plate has a thickness of 0.15 cm to 1 cm;
   wherein a plurality of enamel block substrates are mounted on the first major surface of the plate and arranged in an array, the enamel block substrates each having a mass of heated wax material applied to a surface of the substrate to be pressed against the first major surface of the plate, and
   wherein the elongated rod-shaped handle includes a diameter that is substantially smaller than a width of the plate.

15. A method of claim 14, wherein the apparatus is left in the oral cavity of the subject for a period of time between about 2 minutes to about 2 hours.

\* \* \* \* \*